United States Patent
Ruan et al.

(10) Patent No.: US 10,975,048 B2
(45) Date of Patent: Apr. 13, 2021

(54) COMPOSITION OF 1,3,4-SELENADIAZOLE CONTAINING COMPOUNDS WITH PHARMACOLOGICAL ACTIVITY

(71) Applicant: HANGZHOU JENNIFER BIOTECH CO., LTD, Hangzhou (CN)

(72) Inventors: Benfang Helen Ruan, Hangzhou (CN); Jennifer Jin Ruan, Hangzhou (CN)

(*) Notice: Subject to any disclaimer, the term of this patent is extended or adjusted under 35 U.S.C. 154(b) by 0 days.

(21) Appl. No.: 16/009,106

(22) Filed: Jun. 14, 2018

(65) Prior Publication Data

US 2018/0290991 A1 Oct. 11, 2018

Related U.S. Application Data

(63) Continuation-in-part of application No. PCT/CN2016/109975, filed on Dec. 14, 2016.

(30) Foreign Application Priority Data

Dec. 14, 2015 (CN) .......................... 201510929374.6

(51) Int. Cl.

| C07D 293/06 | (2006.01) |
|---|---|
| C07D 421/06 | (2006.01) |
| C07D 421/12 | (2006.01) |
| A61K 31/41 | (2006.01) |
| A61K 31/4439 | (2006.01) |
| A61K 31/454 | (2006.01) |
| A61K 31/4545 | (2006.01) |
| A61K 31/501 | (2006.01) |
| A61K 45/06 | (2006.01) |
| C07D 421/04 | (2006.01) |
| C07D 421/14 | (2006.01) |

(52) U.S. Cl.
CPC ............ *C07D 293/06* (2013.01); *A61K 31/41* (2013.01); *A61K 31/4439* (2013.01); *A61K 31/454* (2013.01); *A61K 31/4545* (2013.01); *A61K 31/501* (2013.01); *A61K 45/06* (2013.01); *C07D 421/04* (2013.01); *C07D 421/06* (2013.01); *C07D 421/12* (2013.01); *C07D 421/14* (2013.01)

(58) Field of Classification Search
None
See application file for complete search history.

(56) References Cited

U.S. PATENT DOCUMENTS

| 6,093,532 A | 7/2000 | Erdelmeier et al. |
| 6,525,040 B1 | 2/2003 | Erdelmeier et al. |
| 2005/0227957 A1 | 10/2005 | Murphy et al. |

FOREIGN PATENT DOCUMENTS

| CN | 102285944 A | 12/2011 |
| CN | 102766111 A | 11/2012 |
| CN | 106866581 A | 6/2017 |
| EP | 1323714 A1 | 7/2003 |

OTHER PUBLICATIONS

M. Al-Ghorbani, "In vitro antioxidant potential study of triazole and thiadiazole analogues", from Journal of Chemical and Pharmaceutical Research, pp. 1-7, published Dec. 31, 2013.
From PCT/CN 2016/109975, International Preliminary Report on Patentability, dated Jun. 19, 2018.
From PCT/CN 2016/109975, International Search Report dated Feb. 16, 2016.
From PCT/CN 2016/109975, Written Opinion of the International Searching Authority dated Feb. 16, 2017.
From CN201510929374.6, Chinese office action dated Aug. 28, 2018 with English translation from Global Dossier.
From CN201510929374.6, Chinese search report dated Aug. 28, 2018.
Shaifee, A. et al., "Selinium hetrocylces VIII: Synthesis and antibacterial activity of selenosemicarbazied and 1,3,4-Selenadiaszolylcarbamic acid esters", from Journal of Pharmaceutical Sciences, pp. 839-840, published May 1973.

*Primary Examiner* — Jeffrey S Lundgren
*Assistant Examiner* — Michael J Schmitt
(74) *Attorney, Agent, or Firm* — Bayramoglu Law Offices LLC

(57) ABSTRACT

The invention belongs to the field of biomedical research involving the 1,3,4-selenyldiazo derivatives that have cell protective activity. Because there are not so many heterocyclic selenium compounds, we synthesized a new type of selenium analog of BPTES. As the isoacceptor of BPTES, the compounds have antitumor activity, anti-oxidation and cell protection function. Currently many drugs contain the thiodiazo motif, so synthesis of selenyldiazo functional group could further optimize these drugs and are important in new drug development and application.

6 Claims, 1 Drawing Sheet

DMSO | Compound 1
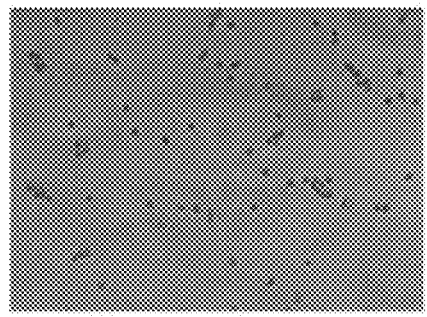 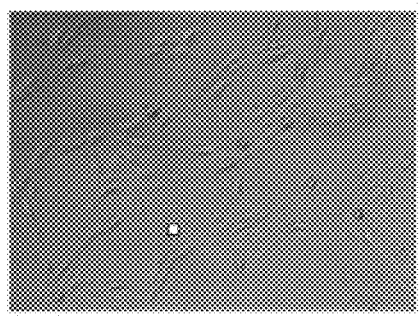
Compound 5 | Compound 9
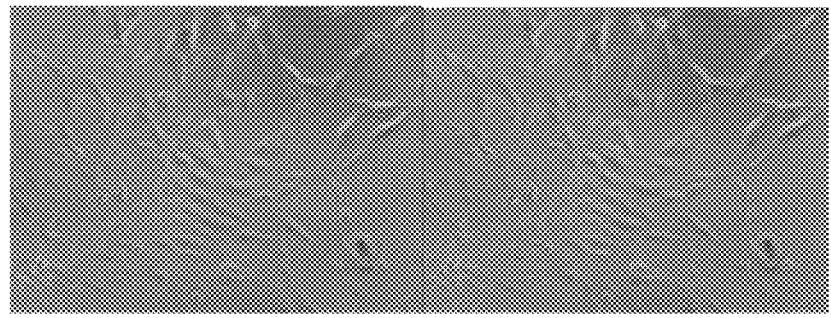
Compound 28 | Compound 17
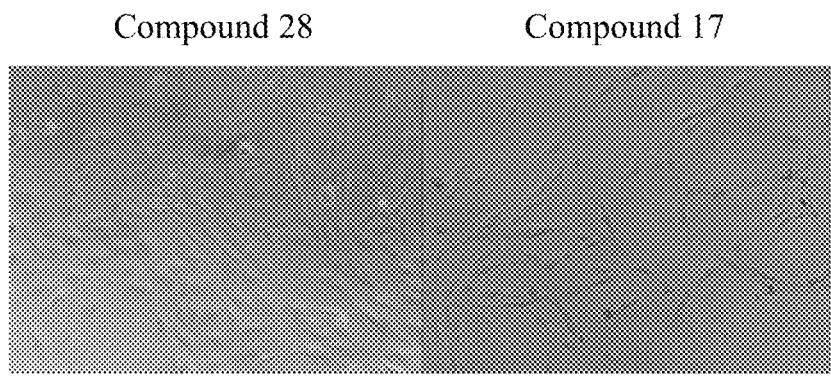

COMPOSITION OF 1,3,4-SELENADIAZOLE CONTAINING COMPOUNDS WITH PHARMACOLOGICAL ACTIVITY

The present application is a Continuation-in-Part Application of PCT Application No. PCT/CN2016/109975 filed on Dec. 14, 2016, which claims priority to the Chinese Patent Application No. 201510929374.6 filed on Dec. 14, 2015, the disclosures of which are incorporated herein by reference.

FIELD OF INVENTION

This invention relates to the field of pharmaceutical biotechnology, and in particular to a kind of 1,3,4-selenadiazole compounds with pharmacological activity.

BACKGROUND OF THE INVENTION

The selenium-containing heterocycle has the efficacy of antioxidant, anti-inflammatory, antibacterial, antiviral and antitumor activity. The anti-tumor mechanism of selenium compounds generally includes the following aspects: with cytotoxic effect, scavenging free radicals, blocking the transmission of information of proliferation and division in cancer cells, inducing apoptosis, regulating immune function, inhibiting angiogenesis and changing the process of metabolism of certain carcinogens.

Selenium compounds include selenium-containing heterocycle, diselenide, selenide, selenium cyanide, methyl selenium acid, selenium-containing amino acids (protein), selenium sugar, etc. Selenium-containing heterocyclic compounds are a big group of organic selenium compounds, whose potential pharmacological activities have attracted more and more attention. For example, Ebselen is a kind of small-molecule compound, which most successfully imitated the glutathione peroxidase, has now entered the phase III of clinical study. Selenium cyanide is a class of selenium compounds, and the earliest selenium cyanide was 4-phenylenebi(methylene)selenocyanoate (P-XSC). Selenazole furan has a significant inhibitory effect on the H1210 leukemia of mice and it has also entered the phase I of clinical study. These organic selenium compounds aforesaid have been known to professional researchers and some effects have been obtained in clinical application, however, further improvement is required in anti-oxidation and protection of cell growth.

In view of this, other researchers have developed a kind of 1,2,5-selenadiazole compounds, which showed a great inhibitory effect on MCF-7 human breast cancer cells with both preferable stability and good consequence on cell growth. The comparison experiment showed selenium compounds had lower toxicity to the body weight, liver and kidney of mice, meanwhile, but the poisonousness of selenium on cancer cells was preserved. Therefore, this kind of selenium compounds has better prospects for clinical application.

DESCRIPTION OF THE INVENTION

Because of the limited types of selenium heterocycles and the strong inhibition of BPTES (thiadiazole) on the growth of tumors, we synthesized selenadiazole compounds substituted by various functional groups through new synthetic methods. Furthermore, tests of these compounds had been performed to confirm their inhibitory effects on the tumor, antioxidant activity and cytoprotective function. In addition, selenadiazole can substitute thiadiazole as its bioisostere and there are many drugs containing thiadiazole. Hence it is remarkably significant to synthesize selenadiazole derivatives with various functional groups and optimize the activity of medicinal thiadiazole compounds, for the development and application of new drugs. At the same time, we also studied a series of reactions of substituted selenourea compounds with substituted carboxylic acids or substituted cyano groups under mild conditions to synthesize selenadiazole. These various substituted selenadiazole derivatives including aromatic derivatives and so on, have good antioxidant effect.

The objective of this invention is to provide a series of 1,3,4-selenadiazole compounds with pharmacological activity, preferable stability and good activity on the growth of cells. These compounds have the structure as follows:

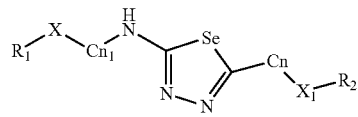

Wherein:

$R_1$, and $R_2$ are independent substituents comprising 1 to 20 atoms selected from the group of C, H, N, O, S, P, Si and halogen atoms, which include aromatic ring, aromatic heterocycle, substituted alkyl, amide, ether, lipid, halogen, silane, thioether, amine, phosphate group, sulfoxide, sulfonyl, amino acid and carboxyl;

Cn represent $C_1$ to $C_{20}$ carbon chain or $C_1$ to $C_8$ carbon chains optimized;

$Cn_1$ represent $C_1$ to $C_8$ carbon chain;

X is one of N, O, S, P and Si.

As a kind of embodiment, the 1,3,4-selenadiazole compounds with pharmacological activity, have the following structural formula:

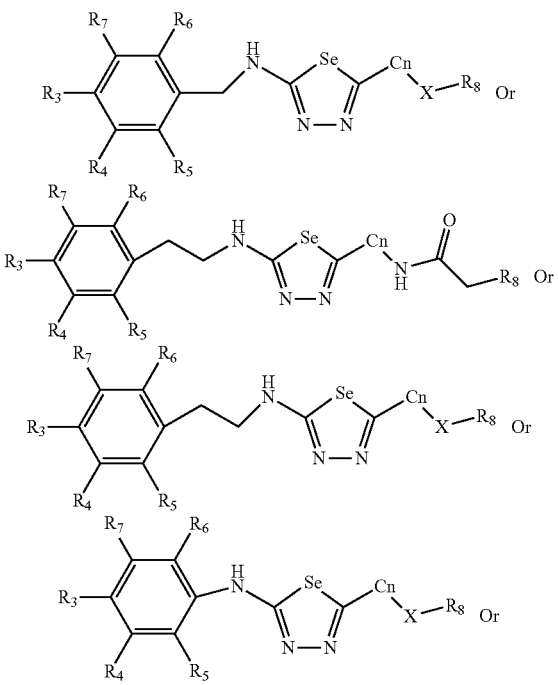

-continued

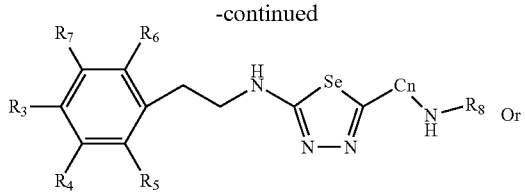

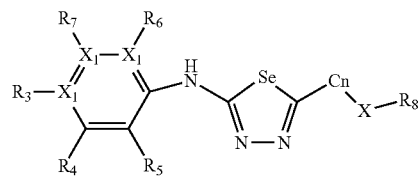

Wherein:

R$_3$, R$_4$, R$_5$, R$_6$, R$_7$, R$_8$ are independent substituents comprising 1 to 20 atoms selected from the group of C, H, N, O, S, P, Si and halogen atoms, which contain hydrogen, aromatic ring, aromatic heterocycle, substituted alkyl, amide, carbonyl, ether, lipid, halogen, silane, thioether, amine, phosphate group, sulfoxide, sulfonyl, amino acid and carboxyl;

X is one of N, O and S.

Preferably, the 1,3,4-selenadiazole compounds with pharmacological activity, have the following structural formula:

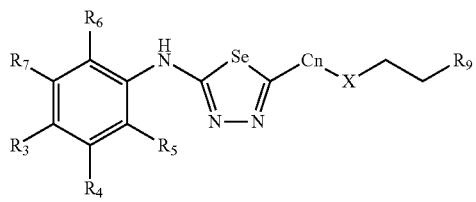

Wherein:

R$_9$ is an independent substituent containing 1 to 20 atoms selected from the group of C, H, N, O, S, P, Si and halogen atoms, which includes aromatic ring, aromatic heterocycle, substituted alkyl, amide, ether, lipid, halogen, silane, thioether, amine, phosphate group, sulfoxide, sulfonyl, amino acid and carboxyl.

Preferably, the 1,3,4-selenadiazole compounds with pharmacological activity, have the following structural formula:

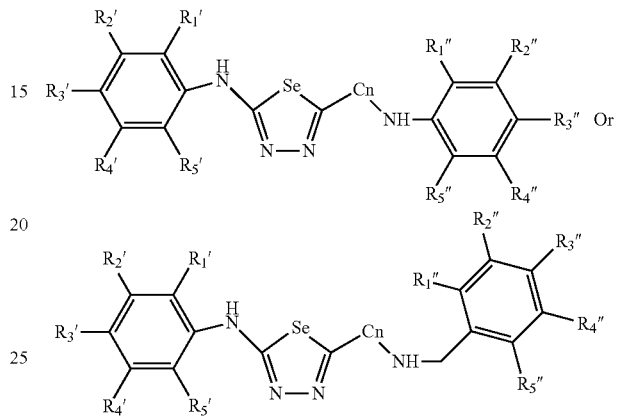

Wherein:

R$_1$', R$_2$', R$_3$', R$_4$', R$_5$', R$_1$", R$_2$", R$_3$", R$_4$", R$_5$" are independent substituents comprising 1 to 50 atoms selected from the group consisting of C, H, N, O, S, P, Si and halogen atoms, which contain hydrogen, aromatic heterocycle, substituted alkyl, amide, ether, lipid, halogen, silane, thioether, amine, phosphate group, sulfoxide, sulfonyl, amino acid and carboxyl.

This invention also provides the 1,3,4-selenadiazole compounds with pharmacological activity, having the following structural formula:

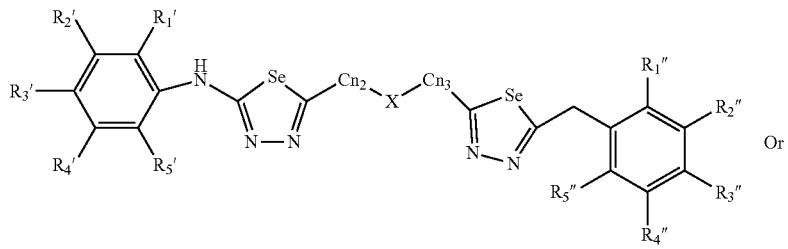

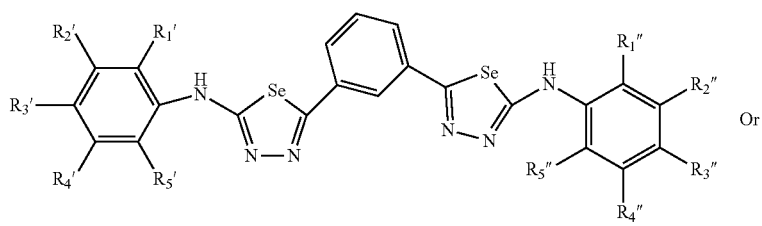

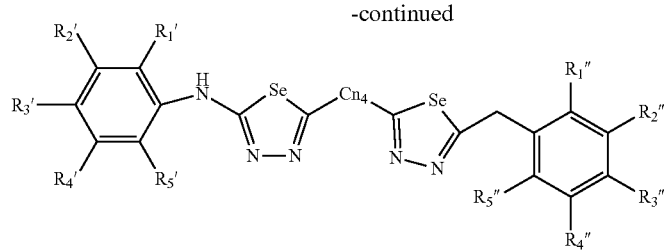

Wherein:

$R_1'$, $R_2'$, $R_3'$, $R_4'$, $R_5'$, $R_1''$, $R_2''$, $R_3''$, $R_4''$, $R_5''$ are independent substituents comprising 1 to 50 atoms selected from the group consisting of C, H, N, O, S, P, Si and halogen atoms, which contain hydrogen, aromatic heterocycle, substituted alkyl, amide, ether, lipid, halogen, silane, thioether, amine, phosphate group, sulfoxide, sulfonyl, amino acid and carboxyl.

$Cn_4$ represents $C_1$ to $C_{20}$ carbon chain;

X is one of N, O, S, P and Si.

Besides, this invention also provides the following compounds:

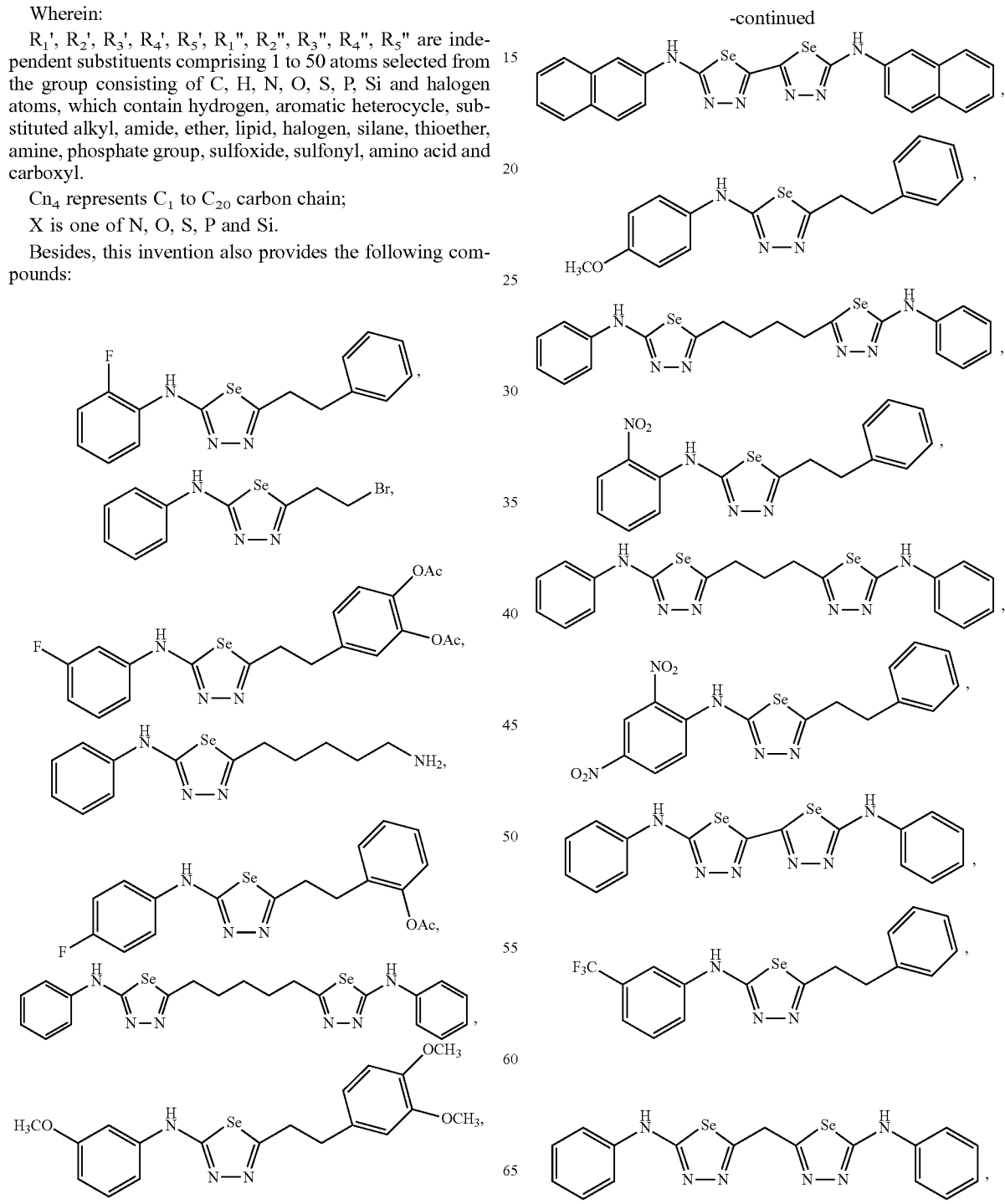

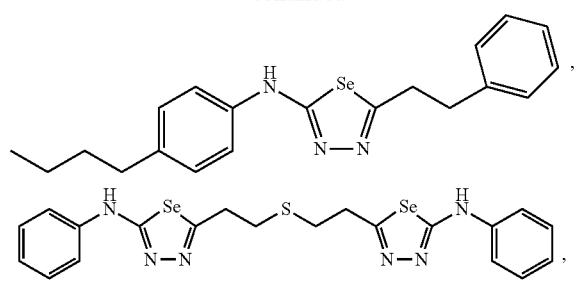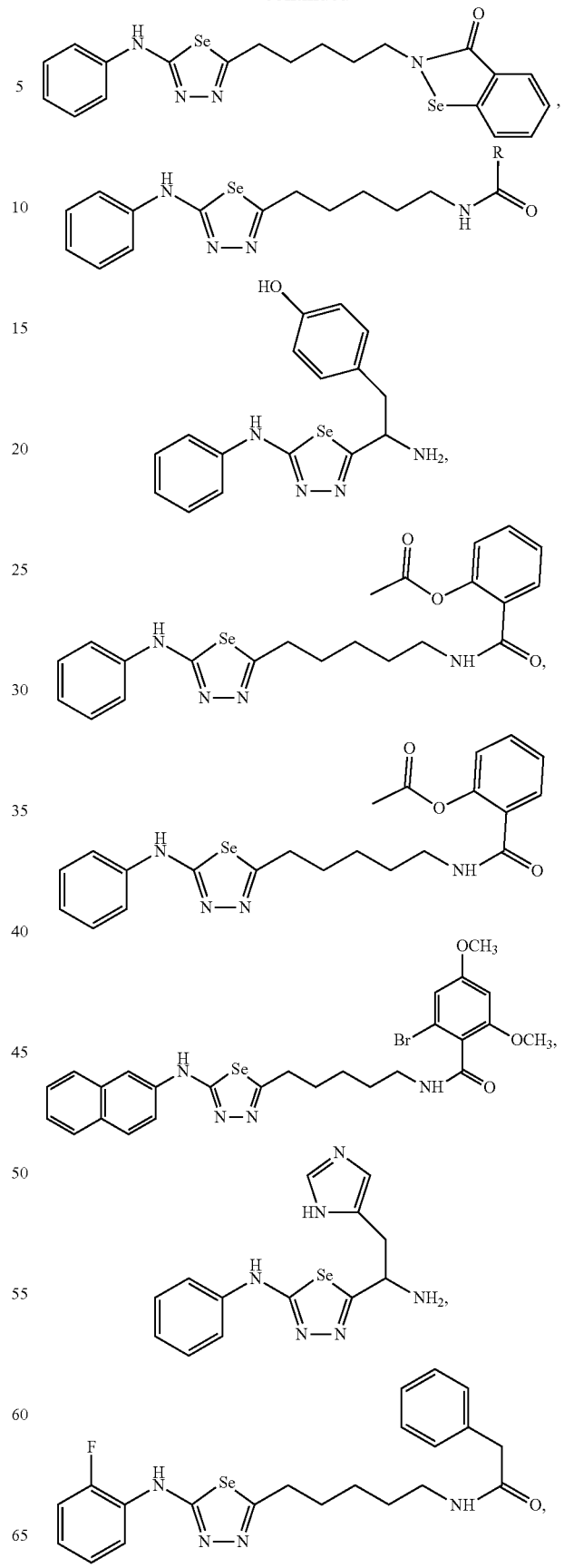

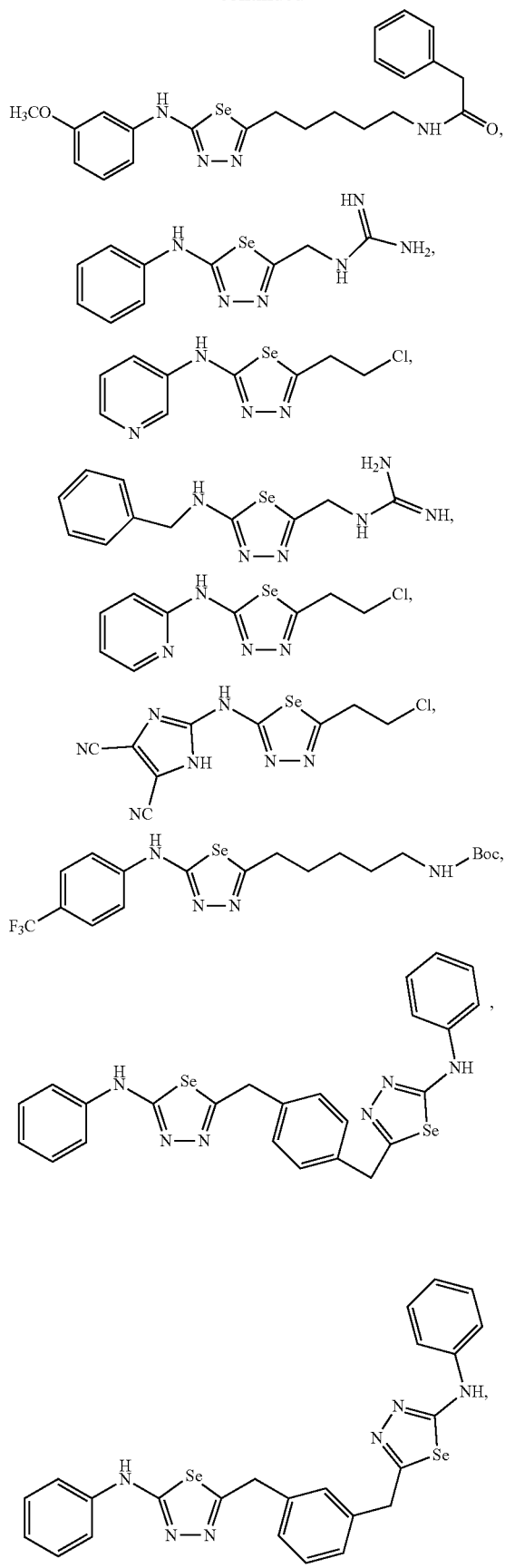

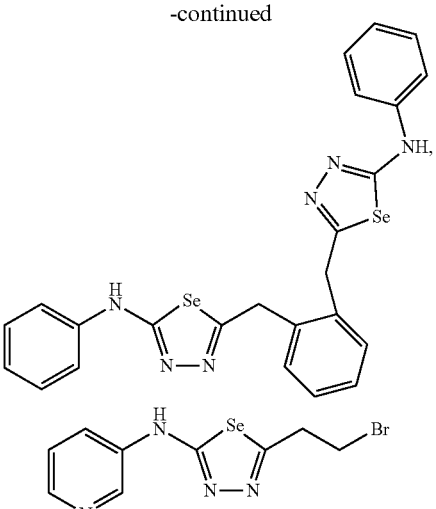

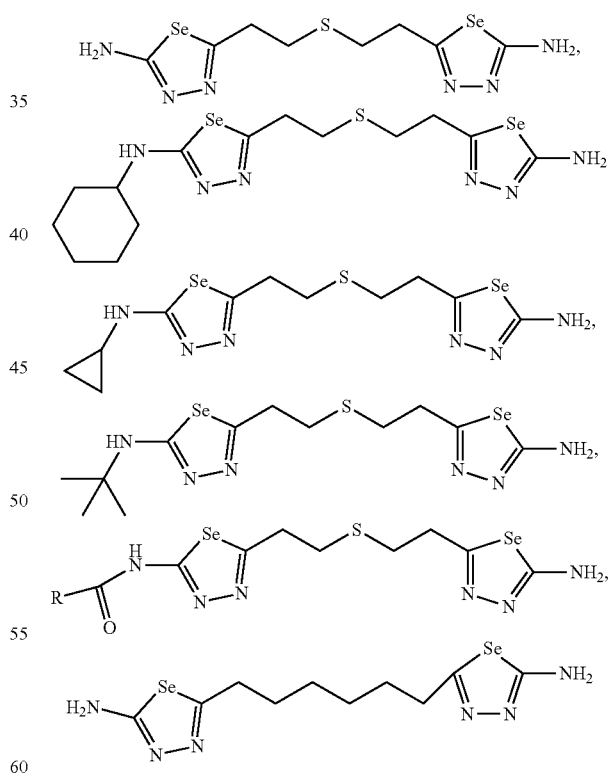

Wherein:
OAc is acetoxy group; Boc is t-butoxycarbonyl; R is a substituent selected from the group of hydrogen, aromatic heterocycle, substituted alkyl, amide, ether, lipid, halogen, silane, thioether, amine, phosphate group, sulfoxide, sulfonyl, amino acid and carboxyl.

In addition, this invention also provides the following examples of structures of specific compounds:

Wherein:
R is a substituent selected from the group containing double bond, ketone, hydroxyl, aromatic ring, aromatic heterocycle, naphthenic base, substituted alkyl, amide, ether, lipid, halogen, silane, thioether, amine, phosphate group, sulfoxide, sulfonyl, amino acid and carboxyl.

X is selected from C, N, O, S, Si, Se, double bond, ketone, hydroxyl, aromatic ring, aromatic heterocycle, naphthenic base, substituted alkyl, amide, ether, lipid, halogen, silane, thioether, amine, phosphate group, sulfoxide, sulfonyl.

In addition, this invention also provides another kind of 1,3,4-selenadiazole compound with pharmacological activity, having the following structural formula:

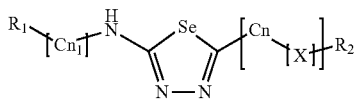
I

Wherein:

$R_1$ and $R_2$ are functional groups, selected from the group including one or several aromatic rings, aromatic heterocycles, substituted alkyls, amides, ethers, lipids, halogens, silanes, thioethers, amines, phosphate groups, sulfoxides, sulfonyls, amino acids and carboxyls;

Cn is $C_1$ to $C_{20}$ carbon chain;

Cn1 is $C_1$ to $C_8$ carbon chain.

X is selected from the group consisting of benzene rings or functional groups or groups containing one or more heteroatoms selected from N, O, S, P, Si.

The preparation of the above exemplified structural formulas can be performed from the corresponding precursors by following the procedure described in the examples below.

It should be noted that the expression "[ ]" included in the general formula of the present application means that the structure therein may be omitted.

$R_1$ has the structure of formula II:

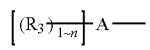
II

The A is an aromatic ring containing one or more heterocycles with 4-5 heteroatoms selected from N, O, S.

$(R_3)_{1\sim n}$ are one or more functional group or groups independently connected to the substitutable positions of A (aromatic ring); the $R_3$, attached to a differently or identically substitutable position of A, is independently selected from the group consisting of aromatic ring, aromatic heterocycle, substituted alkyl, amide, ether, lipid, halogen, silane, thioether, amine, phosphate group, sulfoxide, sulfonyl, amino acid, carboxyl, acetic acid and alkoxy; and n is the number of replaceable locations of A.

Furthermore, A could be selected from aromatic ring, pyridine, imidazole, naphthalene, heterocyles containing 1~3 heteroatoms; the heteroatoms could be selected from N, O, S.

Further, for the right-hand part of the structure of the formula 1, $R_2$ is W1 substituted group where the W1 substituents could be selected from aromatic ring, aromatic heterocyclic substituted alkyl, ether, amide, lipid, halogen, silane, sulfide, amine, phosphate group, sulfoxide, sulfonyl, amino acids, —COOH.

Or, $R_2$ is H or benzene or naphthalene with 1 or more W2 substituted, W2 is selected from the functional groups such as aromatic rings with or without heteroatoms, cyclic rings with heteroatooms, alkyl, amide, ether, lipids, halogen, silane, sulfide, amine, phosphate group, sulfoxide, sulfonyl, amino acids —COOH.

In addition, $R_2$ has the following general structure:

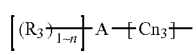
III

Among them, the A is selected from benzene or piperidine; $Cn_3$ is selected from 1~20 carbon chain;

$(R_3)_{1\sim n}$ are one or more functional groups or groups independently connected to the substitutable positions of A (aromatic ring); the $R_3$, attached to a differently or identically substitutable position of A, is independently selected from the group consisting of aromatic ring, aromatic heterocycle, substituted alkyl, amide, ether, lipid, halogen, silane, thioether, amine, phosphate group, sulfoxide, sulfonyl, amino acid, carboxyl, acetic acid and alkoxy; and n is the number of replaceable locations of A.

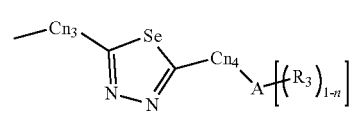
IV

Among them, $Cn_3$ is selected from 1~20 carbon carbon chain or benzene ring; $Cn_4$ is selected from 1~20 carbon chain or —NH—;

A is a benzene ring;

$(R_3)_{1\sim n}$ are one or more functional group or groups independently connected to the substitutable positions of A (aromatic ring); the $R_3$, attached to a differently or identically substitutable position of A, is independently selected from the group consisting of aromatic ring, aromatic heterocycle, substituted alkyl, amide, ether, lipid, halogen, silane, thioether, amine, phosphate group, sulfoxide, sulfonyl, amino acid, carboxyl, acetic acid and alkoxy; and n is the number of replaceable locations of A.

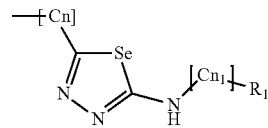
V

The $R_1$ contains one or more aromatic rings, aromatic heterocyclic substituted alkyl, ether, amide, lipid, halogen, silane, sulfide, amine, phosphate group, sulfoxide, sulfonyl, amino acids, —COOH functional groups;

Cn is a carbon chain containing 0~20 carbon;

$Cn_1$ is a carbon chain containing 0~8 carbon.

In addition, the general formula I, X contains one or more functional groups or X1 groups, respectively. X1 can independently selected from —NH—, —S—, selendiazo, —S—, amide.

In addition, the present invention discovered that the compound mentioned above has antioxidant and cell protective activities.

The 1,3,4-selendiazo compounds of the present application are prepared as follows:

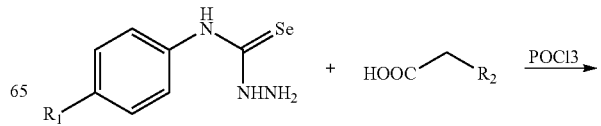

-continued

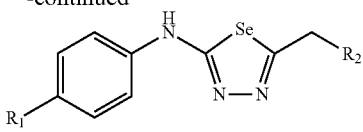

Preparation process of phenyl selenourea is exemplified as follows:

The mixture of phenyl selenourea (1 mmol; or other selenourea), carboxylic acid compounds (0.2-4 mmol), and 5 ml of POCl3 was stirred homogeneously. Then the mixture was heated to 50-80° C. and reacted for 0.5-12 hours. After that, stopped heating in oil bath, the reaction solution was dried under reduced pressure, then separated by column chromatography and dried. The product was obtained with a yield of 40-95%.

The preparation method using selenourea and cyano compounds is as follows:

Selenourea (1 mmol; or other selenium urea), propionitrilethioeither (0.2~4, mmol) and 5 ml TFA are mixed. Heating up to 50~80° C., reaction 0.5~12 h, stop the oil bath heating, concentrate the reaction solution under reduced pressure, column chromatography separation, dry. Product yield: 40~95%.

DESCRIPTION OF DRAWINGS

This application has 1 illustration:

FIG. 1. Schematic diagram of the antioxidant activity of related compounds in the present invention.

EXAMPLES

Without special notice, the terminology used in this invention has the following general implications:

The sign [ ] indicates that the contents in [ ] can be omitted or removed. After omitting or removing, the groups on both sides of [ ] can be directly connected by chemical bonds. The term "halogen" or "halogen atom" means a halogen substituent, the fluorine (—F), the chlorine group (—Cl), the bromine group (—Br) or the iodine group (—I); the term "halogen" is replaced by the halogen substituent.

The term "alkyl" refers to the straight chain, branched alkyl chain or cycloalkyl. The "alkyl" is refers to both single ended free alkyl bond such as but not limited to: methyl, ethyl, propyl, isopropyl, butyl, primary/secondary/tertiary butyl, cyclopropyl, methyl cyclopropyl, and cyclobutyl et al, but also include alky that meet the bond valence theory with two or more than two alkyl, refer to but not limited to: —CH₂—, —(CH₂)₂—, —(CH₂)₃—, —(CH₂)₄—, —C(CH₃) (CH₂)₂—.

The term "cyclic hydrocarbons" refers to a ring of at least 3 carbons or with functional group substitutions; in the absence of any opposite meaning, any of the carbon atom can be substituted by another hetero atom containing group to form a new group or a functional group.

The term "heterocyclic ring" refers to a ring contains at least 2 carbons and other hetero atoms or functional groups.

The term "selen" refers to the

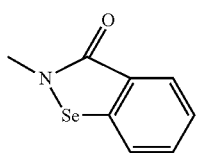

group containing molecular, or with additional group or functional group which is referred as selen derivatives.

The term "oxyalkyl" refers to the substituent can include different alkyl, for example but not limited to all kind of straight chain, branched alkyl chain or cycloalkyl alkyl, similar to that is described for "the alkyl" above.

The term "substitution" refers to the substitution of a hydrogen atom by other functional groups or substituents.

The term "nitrophenyll" refers to at least 2 hydrogen atoms on the benzene are replaced by nitro, hydrogen atoms are substituted by the unknown can choose, for example, but not limited to, a para and ortho.

The term "aromatic" refers to aromatic ring with substituents; no other specific, the aromatic ring could either carbocyclic aryl, or heterocyclic aryl including but not limited to N, S and O atoms; can be monocyclic aryl; can also be fused ring aryl, or polycyclic aryl ring and non fused aryl ring substituents.

The term "heterocyclic" or "aromatic heterocyclic ring" refers to functional groups or substituents derived from the aromatic rings of N, S, O, or other atoms, which vary in quantity.

The term "amide" refers to a functional group or substituent containing an amide bond —CONH—.

The term "carbonyl" refers to a functional group or substituent containing the C=O double bond.

The term "Ether" refers to a functional group or group containing —O—.

The term "ester" refers to a functional group or group containing —COO—, or its derivatives.

The term "silane" refers to a compound or derivative of the Si—H bond.

The term "sulfur ether" refers to a compound containing the same R, wherein R—S—R is an alkyl group.

The term "phosphoric acid group" refers to a functional group or substituent containing —PO4, —HPO4, or —H2PO4.

The term "sulfinyl" refers to a functional group or substituent containing —S=O—.

The term "sulfonyl" refers to a functional group or substituent containing —S(=O)₂.

The term "amino acid" refers to a group of functional groups or substituents that contain both amino and carboxyl groups.

The present invention is further illustrated by the following examples.

Example 1

5-(2-bromoethyl)-N-phenyl-1,3,4-selenadiazol-2-amine (Compound 1)

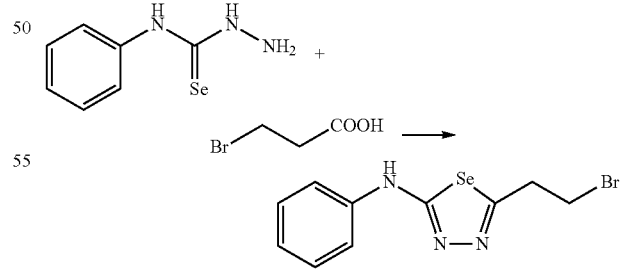

m/z 332 (100%, M+H⁺)

¹H NMR (500 MHz,) δ 10.37 (s, 1H), 7.65-7.53 (m, 2H), 7.35 (d, J=9.0 Hz, 2H), 6.99 (dt, J=7.4, 3.7 Hz, 1H), 3.6 (t, J=6.5 Hz, 2H), 3.38-3.29 (t, J=6.5 Hz, 2H)

To further explore the reaction conditions on the yield of reaction, a group of reactants in different reaction conditions were explored, the specific reaction data are as follows:

| No. | Benzamide Selenide(ml) | 3-Bromopropionic acid(mmol) | Oil of vitriol(ml) | Phosphorus oxychloride(ml) | Proceeding Temp. (° C.) | Time (h) | Crude yield (%) |
|---|---|---|---|---|---|---|---|
| 1 | 44 | 37 | 14 | | 100-120 | 2 | 8% |
| 2 | 44 | 37 | 15 | | 100-140 | 2 | |
| 3 | 44 | 37 | 15 | | 120-126 | 4 | 14% |
| 4 | 44 | 37 | 15 | | 100-110 | 7 | 10% |
| 5 | 44 | 37 | 15 | | 100-130 | 3 | 2% |
| 6 | 44 | 37 | 15 | | 110-120 | 3 | 17% |
| 7 | 44 | 37 | 15 | | 120 | 1.5 | 3% |
| 8 | 44 | 37 | 15 | | 115-125 | 3 | 3% |
| 9 | 44 | 37 | 15 | | 115-120 | 5.5 | 1% |
| 10 | 44 | 37 | 15 | | 115-120 | 3 | 27% |
| 11 | 44 | 37 | 15 | | 115 | 3 | 23% |
| 12 | 44 | 37 | | 15 | 80 | 2 | 53% |
| 13 | 44 | 37 | | 15 | 90-100 | 2.5 | 45% |
| 14 | 44 | 37 | | 15 | 90 | 2.5 | 36% |
| 15 | 44 | 37 | | 15 | 80-85 | 5 | 26% |
| 16 | 44 | 37 | | 15 | 101-107 | 1 | 30% |
| 17 | 44 | 37 | | 15 | 81.3-84.0 | 1 | 39% |
| 18 | 44 | 37 | | 15 | 80-84.8 | 2 | 22% |
| 19 | 44 | 37 | | 15 | 100-110 | 1 | 12% |
| 20 | 44 | 37 | | 15 | <110 | 2 | 19% |
| 21 | 22 | 19 | | 6 | 75-80 | 3 | 24% |
| 22 | 176 | 148 | | 60 | 80 | 1 | 47% |
| 23 | 22 | 19 | | 3 | 75-80 | 3 | 45% |
| 24 | 44 | 37 | | 15 | 90 | 1 | 30% |
| 25 | 44 | 37 | | 15 | 100-80 | 1.5 | 25% |
| 26 | 44 | 37 | | 15 | 90-70 | 1.5 | 42% |
| 27 | 44 | 37 | | 15 | 80-60 | 1.5 | 35% |
| 28 | 44 | 37 | | 10 | 60-50 | 1.5 | 80% |
| 29 | 53 | 30 | | 8 | 50-40 | 1.5 | 50% |
| 30 | 44 | 37 | 5 | 10 | 100-85 | 3 | 45% |
| 31 | 44 | 37 | | 18 | 90-70 | 3 | 85% |
| 32 | 44 | 37 | | 15 | 80-60 | 3 | 95% |
| 33 | 220 | 185 | | 75 | 60-50 | 3 | 84% |
| 34 | 44 | 37 | | 15 | 60-40 | 6 | 85% |

A variety of different reactants and the reaction equation are listed as follows. Emphasized here is that the reaction conditions are essentially the same: selenyl urea carboxylic acid or cyanide compounds (0.2~4 mmol), and 5 ml $POCl_3$ are mixed and reacted at 50 to 80° C. for 0.5~12 h, normal workup to yield selenyldiazo 40-95%; The methods are applicable to other listed compounds in the claim.

5-(2-bromoethyl)-N-(pyridin-3-yl)-1,3,4-selenadiazol-2-amine (Compound 2)

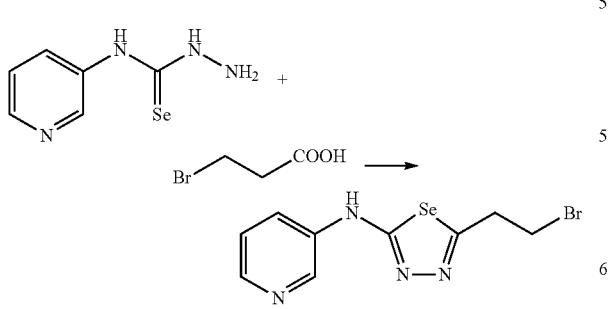

m/z 333 (100%, M+H$^+$)

$^1$H NMR (500 MHz,) δ 10 (s, 1H), 8.9 (s, 1H), 8.1 (d, J=9.0 Hz, 2H), 7.3 m, 1H), 3.6 (t, J=6.5 Hz, 2H), 3.38-3.29 (t, J=6.5 Hz, 2H)

5-(2-chloroethyl)-N-phenyl-1,3,4-selenadiazol-2-amine (Compound 3)

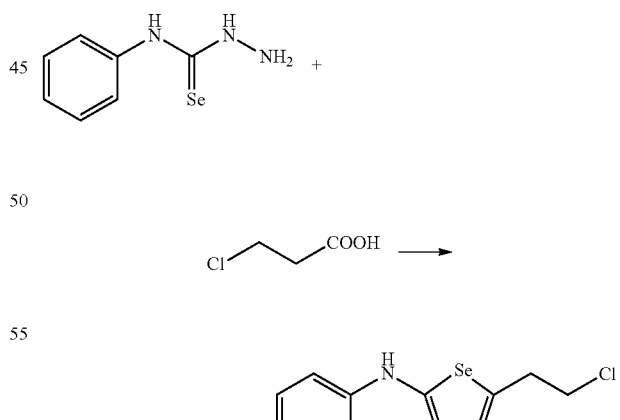

Mp: 109-110° C.

m/z 288 (100%, M+H$^+$)

$^1$H NMR (500 MHz,) δ 10.37 (s, 1H), 7.65-7.53 (m, 2H), 7.35 (d, J=9.0 Hz, 2H), 6.99 (dt, J=7.4, 3.7 Hz, 1H), 3.96 (t, J=6.5 Hz, 2H), 3.38 (t, J=6.5 Hz, 2H)

N-benzyl-5-(2-chloroethyl)-1,3,4-selenadiazol-2-amine (Compound 4)

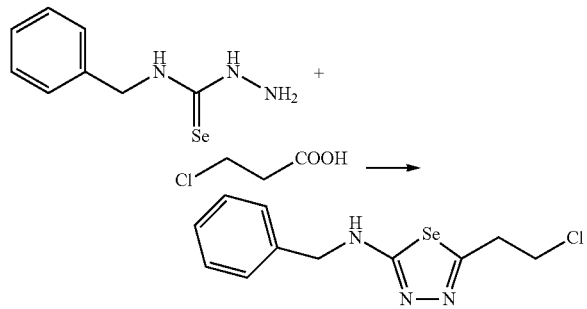

Mp: 109-110° C.
m/z 302 (100%, M+H⁺)
¹H NMR (500 MHz,) δ 9 (1H), 7.65-7.53 (m, 2H), 7.35 (d, J=9.0 Hz, 2H), 6.99 (dt, J=7.4, 3.7 Hz, 1H), 3.96 (m, J=6.5 Hz, 4H), 3.38-3.29 (t, J=6.5 Hz, 2H)

5-(2-chloroethyl)-N-phenethyl-1,3,4-selenadiazol-2-amine (Compound 5)

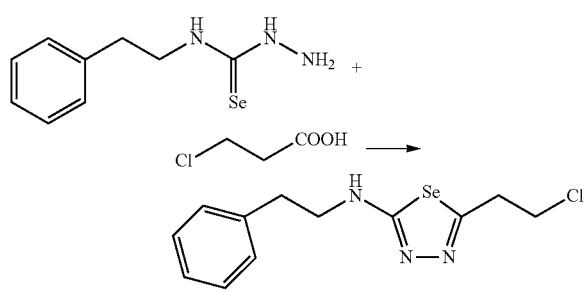

Mp: 109-110° C.
m/z 316 (100%, M+H⁺)
¹H NMR (500 MHz,) δ 9 (1H), 7.65-7.53 (m, 2H), 7.35 (d, J=9.0 Hz, 2H), 6.99 (dt, J=7.4, 3.710 Hz, 1H), 3.6 (m, J=6.5 Hz, 4H), 3.38-3.29 (t, J=6.5 Hz, 4H)

4-(2-((5-(2-chloroethyl)-1,3,4-selenadiazol-2-yl)amino)ethyl)-1,2-phenylene diacetate (Compound 6)

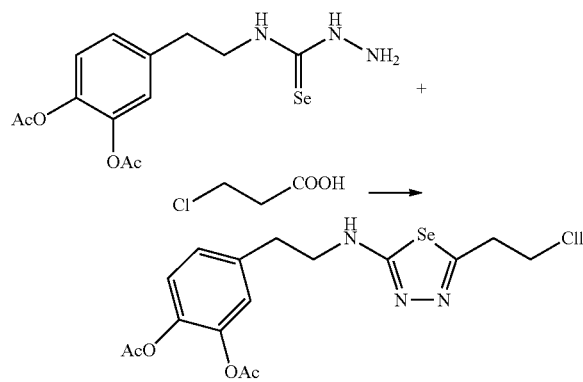

Mp: 109-110° C.
m/z 316 (100%, M+H⁺)
¹H NMR (500 MHz,) δ 9 (1H), 7.65-7.53 (m, 3H), 3.6 (m, J=6.5 Hz, 4H), 3.38-3.29 (t, J=6.5 Hz, 4H), 2.4 (s, 6H)

1-((5-(phenylamino)-1,3,4-selenadiazol-2-yl)methyl)guanidine (Compound 7)

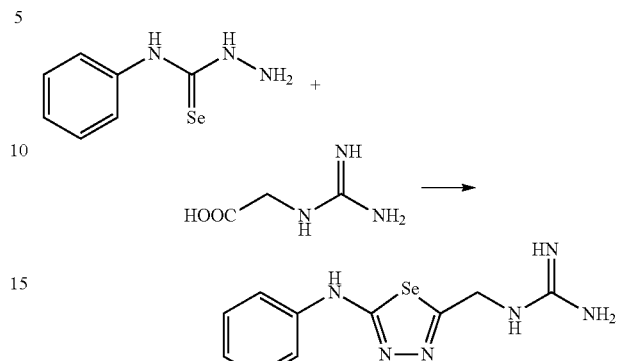

Mp: 109-110° C.
m/z 296 (100%, M+H⁺)
¹H NMR (500 MHz,) δ 10.6 (1H), 7.65-7.53 (m, 2H), 7.35 (d, J=9.0 Hz, 2H), 6.99 (dt, J=7.4, 3.7 Hz, 1H), 3.2 (2H)

5,5'-(thiobis(ethane-2,1-diyl))bis(N-phenyl-1,3,4-selenadiazol-2-amine) (Compound 8)

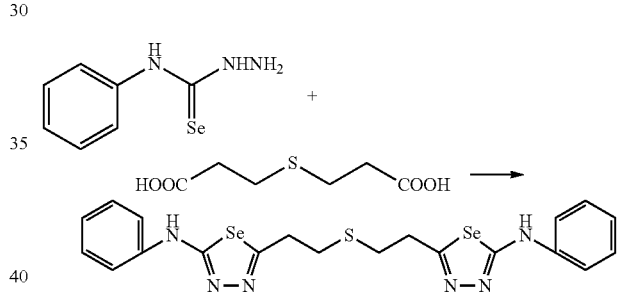

Mp=172-174° C., m/z 534.4 (100%, M+H⁺)
¹H NMR (500 MHz, DMSO-d6) δ 10.37 (d, J=70.4 Hz, 2H), 7.65-7.53 (m, 4H), 7.35 (d, J=9.010 Hz, 4H), 6.99 (dt, J=7.4, 3.7 Hz, 2H), 3.24 (t, J=7.2 Hz, 2H), 3.06 (t, J=7.2 Hz, 2H), 2.88 (dt, J=27.2, 7.2 Hz, 4H)

N5,N5'-diphenyl-[2,2'-bi(1,3,4-selenadiazole)]-5,5'-diamine (Compound 9)

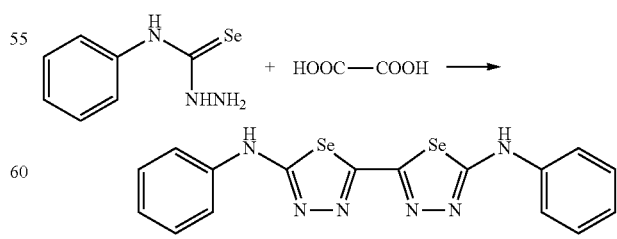

m/z 447 (100%, M+H⁺)
¹H NMR (500 MHz,) δ 10.26 (s, 2H), 7.58 (dd, J=30.9, 7.6 Hz, 4H), 7.33 (t, J=7.9 Hz, 4H), 6.99 (t, J=7.3 Hz, 2H)

5,5'-methylenebis(N-phenyl-1,3,4-selenadiazol-2-amine) (Compound 10)

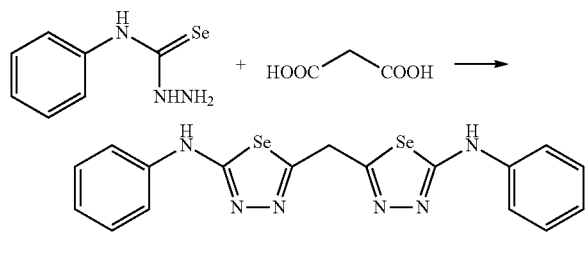

Mp=130-132° C.
m/z 461 (100%, M+H⁺)
¹H NMR (500 MHz,) δ 10.15 (s, 2H), 7.51 (d, J=8.0 Hz, 4H), 7.24-7.17 (m, 4H), 6.90 (t, J=5.6 Hz, 2H), 3.45-3.35 (s, 2H)

5,5'-(ethane-1,2-diyl)bis(N-phenyl-1,3,4-selenadiazol-2-amine) (Compound 11)

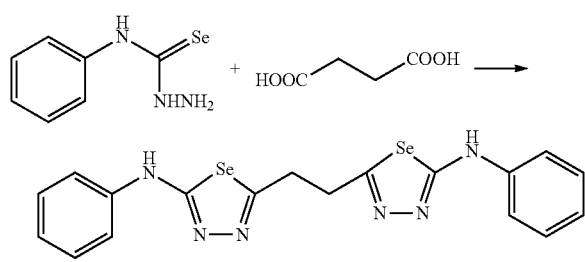

Mp=160-161° C.
m/z 475 (100%, M+H⁺)
¹H NMR (500 MHz,) δ 10.25 (s, 2H), 7.61 (d, J=8.0 Hz, 4H), 7.34-7.27 (m, 4H), 6.98 (t, J=5.610 Hz, 2H), 1.32-1.20 (m, 4H)

5,5'-(propane-1,3-diyl)bis(N-phenyl-1,3,4-selenadiazol-2-amine) (Compound 12)

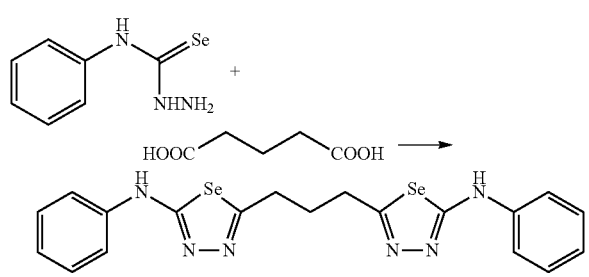

Mp: 198-201° C.
m/z 489 (100%, M+H⁺)
¹H NMR (500 MHz,) δ 9.97 (s, 2H), 7.62 (d, J=8.0 Hz, 4H), 7.33 (t, J=7.5 Hz, 4H), 6.99 (t, J=7.0 Hz, 2H), 3.02 (t, J=7.2 Hz, 4H), 2.15-2.07 (m, 2H)

5,5'-(butane-1,3-diyl)bis(N-phenyl-1,3,4-selenadiazol-2-amine) (Compound 13)

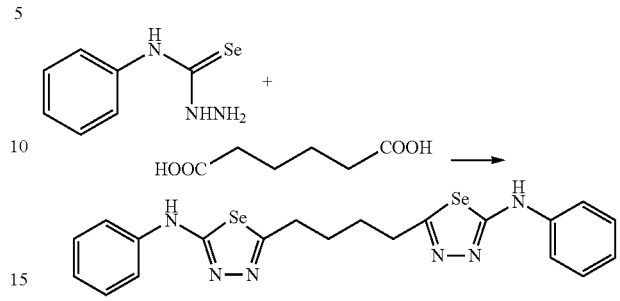

Mp=205-208° C.
m/z 503 (100%, M+H⁺)
¹H NMR (500 MHz,) δ 10.35 (s, 2H), 7.61 (d, J=7.9 Hz, 2H), 7.55 (d, J=8.0 Hz, 2H), 7.33 (t, J=7.6 Hz, 4H), 6.99 (t, J=6.9 Hz, 2H), 3.40 2.96-2.79 (m, 4H), 1.77-1.67 (m, 4H)

5,5'-(pentane-1,5-diyl)bis(N-phenyl-1,3,4-selenadiazol-2-amine) (Compound 14)

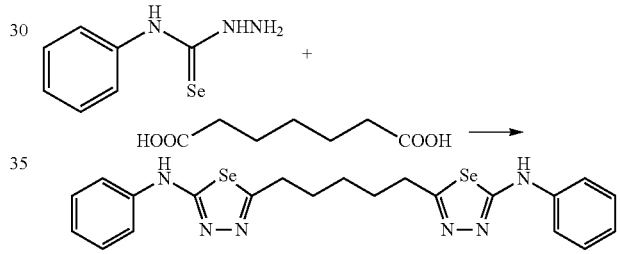

Mp=165-171° C.
m/z 517 (100%, M+H⁺)
¹H NMR (500 MHz,) δ 10.34 (s, 2H), 7.61 (d, J=7.8 Hz, 4H), 7.32 (t, J=7.9 Hz, 4H), 6.98 (t, J=7.3 Hz, 2H), 2.91-2.77 (t, J=7.4 Hz, 4H), 1.77-1.67 (m, 4H), 1.51-1.40 (m, 2H)

methyl 4-(5-(phenylamino)-1,3,4-selenadiazol-2-yl)butanoate (Compound 15)

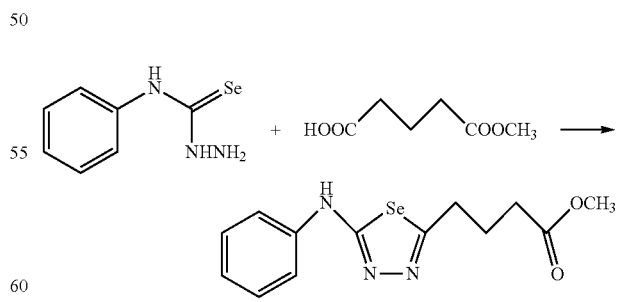

m/z 325 (100%, M+H⁺).
¹H NMR (500 MHz,) δ 10.34 (s, 1H), 7.61 (d, J=7.8 Hz, 2H), 7.32 (t, J=7.9 Hz, 2H), 6.98 (t, J=157.3 Hz, 1H), 3.65 (s, 3H), 2.32 (t, J=7.2 Hz, 2H), 1.9 (m, 2H), 1.5 (t, J=7.2 Hz, 2H)

2-((5-(5-(phenylamino)-1,3,4-selenadiazol-2-yl)pentyl)carbamoyl)phenyl acetate (Compound 16)

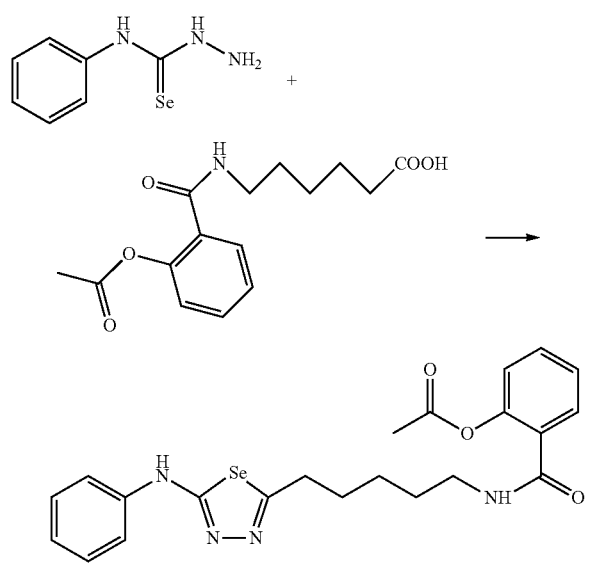

m/z 472 (100%, M+H⁺)
¹H NMR (500 MHz,) δ 10.34 (s, 1H), 7.61-6.98 (m, 9H), 2.4 (s, 3H), 3.18-1.3 (m, 10H),

N-(5-(5-(phenylamino)-1,3,4-selenadiazol-2-yl)pentyl)benzamide (Compound 17)

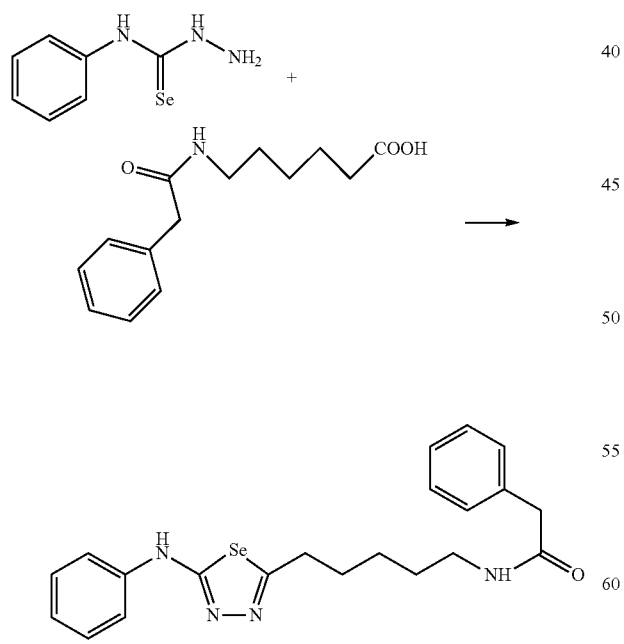

m/z 428 (100%, M+H⁺)
¹H NMR (500 MHz,) δ 10.34 (s, 1H), 7.61-6.98 (m, 10H), 3.19-1.3 (m, 10), tert-butyl(5-(5-(naphthalen-2-ylamino)-1,3,4-selenadiazol-2-yl)pentyl)carbamate (Compound 18)

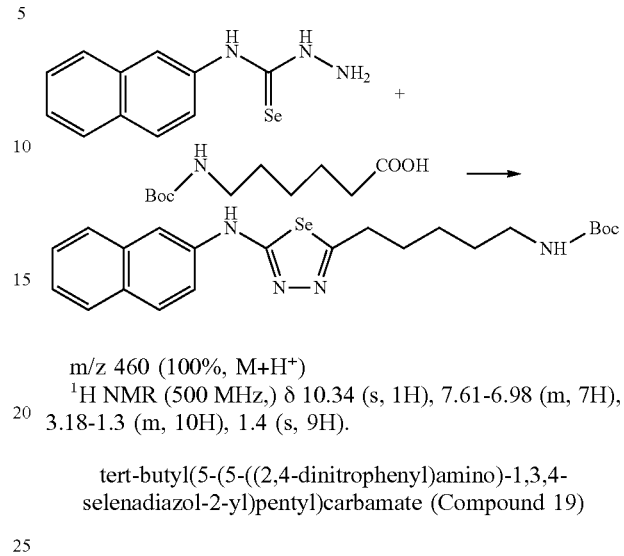

m/z 460 (100%, M+H⁺)
¹H NMR (500 MHz,) δ 10.34 (s, 1H), 7.61-6.98 (m, 7H), 3.18-1.3 (m, 10H), 1.4 (s, 9H).

tert-butyl(5-(5-((2,4-dinitrophenyl)amino)-1,3,4-selenadiazol-2-yl)pentyl)carbamate (Compound 19)

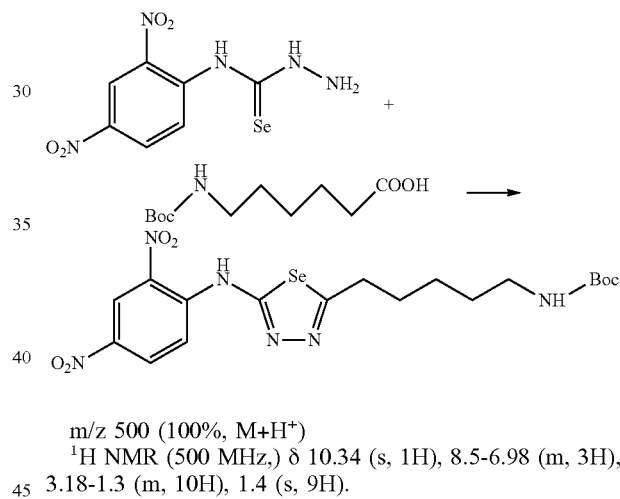

m/z 500 (100%, M+H⁺)
¹H NMR (500 MHz,) δ 10.34 (s, 1H), 8.5-6.98 (m, 3H), 3.18-1.3 (m, 10H), 1.4 (s, 9H).

tert-butyl(5-(5-((2-fluorophenyl)amino)-1,3,4-selenadiazol-2-yl)pentyl)carbamate (Compound 20)

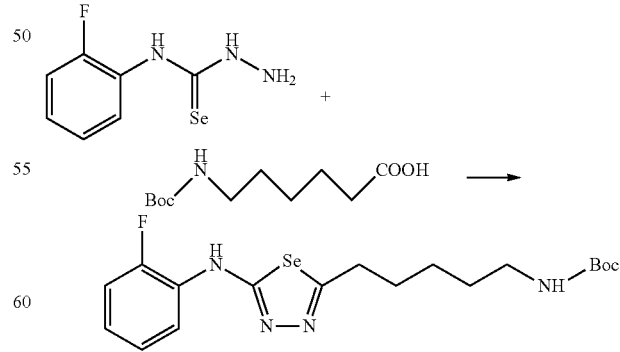

m/z 428 (100%, M+H⁺)
¹H NMR (500 MHz) δ 10.34 (s, 1H), 8.06 (d, J=7.8 Hz, 1H), 7.59 (m, 2H), 7.46 (m, 1H), 7.37 (d, J=8.0, 1H), 3.18-1.3 (m, 10H), 1.4 (s, 9H).

23 tert-butyl(5-(5-((3-((11-oxidanyl)-15-methyl)phenyl)amino)-1,4-selenadiazol-2-yl)pentyl)carbamate (Compound 21)

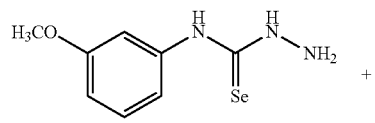

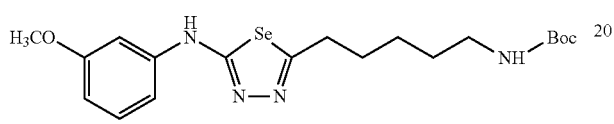

m/z 440 (100%, M+H$^+$)

$^1$H NMR (500 MHz) δ 10.34 (s, 1H), 8.06 (s, J=7.8 Hz, 1H), 7.59 (m, 2H), 7.46 (d, J=8.0, 1H), 7.37 (d, J=8.0, 1H), 3.8 (s, 3H), 3.18-1.3 (m, 10H), 1.4 (s, 9H).

tert-butyl (5-(5-((4-(trifluoromethyl)phenyl)amino)-1,3,4-selenadiazol-2-yl)pentyl)carbamate (Compound 22)

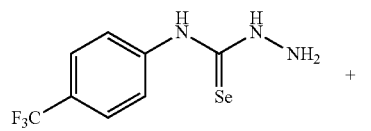

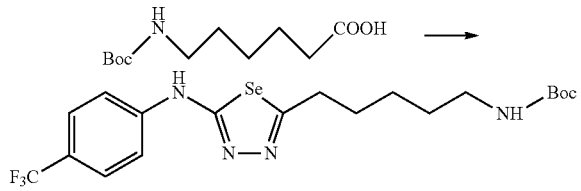

m/z 478 (100%, M+H$^+$)

$^1$H NMR (500 MHz) δ 10.34 (s, 1H), 8.06 (d, J=7.8 Hz, 2H), 7.59 (m, 1H), 7.46 (d, J=7.8, 2H), 3.18-1.3 (m, 10H), 1.4 (s, 9H).

tert-butyl 2-(5-(phenylamino)-1,3,4-selenadiazol-2-yl)pyrrolidine-1-carboxylate (Compound 23)

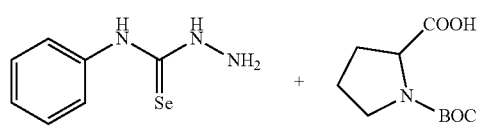

24

-continued

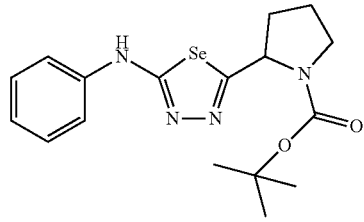

m/z 394 (100%, M+H$^+$)

$^1$H NMR (500 MHz) δ 10.34 (s, 1H), 8.06 (d, J=7.8 Hz, 2H), 7.59-7.46 (m, 3H), 3.4 (m, 3H), 1.7-1.5 (m, 4H), 1.4 (s, 9H).

tert-butyl (2-phenyl-1-(5-(phenylamino)-1,3,4-selenadiazol-2-yl)ethyl)carbamate (Compound 24)

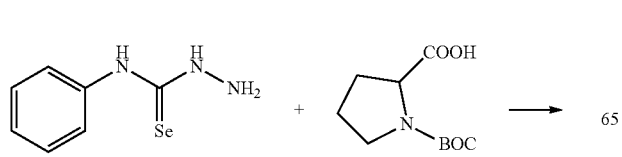

m/z 444 (100%, M+H$^+$)

$^1$H NMR (500 MHz) δ 10.34 (s, 1H), 8.06 (m, J=7.8 Hz, 4H), 7.59-7.46 m, 7H), 4-3.2 (m, 3H), 1.4 (s, 9H).

tert-butyl(1-(5-(phenylamino)-1,3,4-selenadiazol-2-yl)-2-(4-((trimethylsilyl)oxy)phenyl)ethyl)carbamate (Compound 25)

-continued

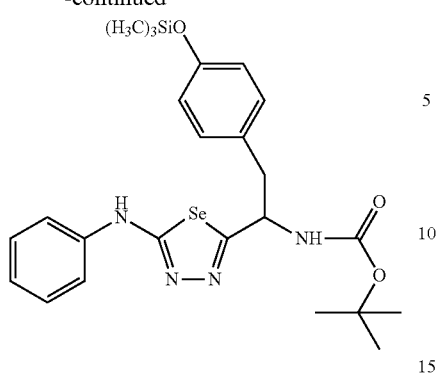

m/z 532 (100%, M+H$^+$)

$^1$H NMR (500 MHz) δ 10.34 (s, 1H), 8.06 (m, J=7.8 Hz, 4H), 7.59-7.46 (m, 6H), 4-3.2 (m, 3H), 101.4 (s, 9H), 0.2 (s, 9H)

tert-butyl(2-(4H-imidazol-5-yl)-1-(5-(phenylamino)-1,3,4-selenadiazol-2-yl)ethyl)carbamate (Compound 26)

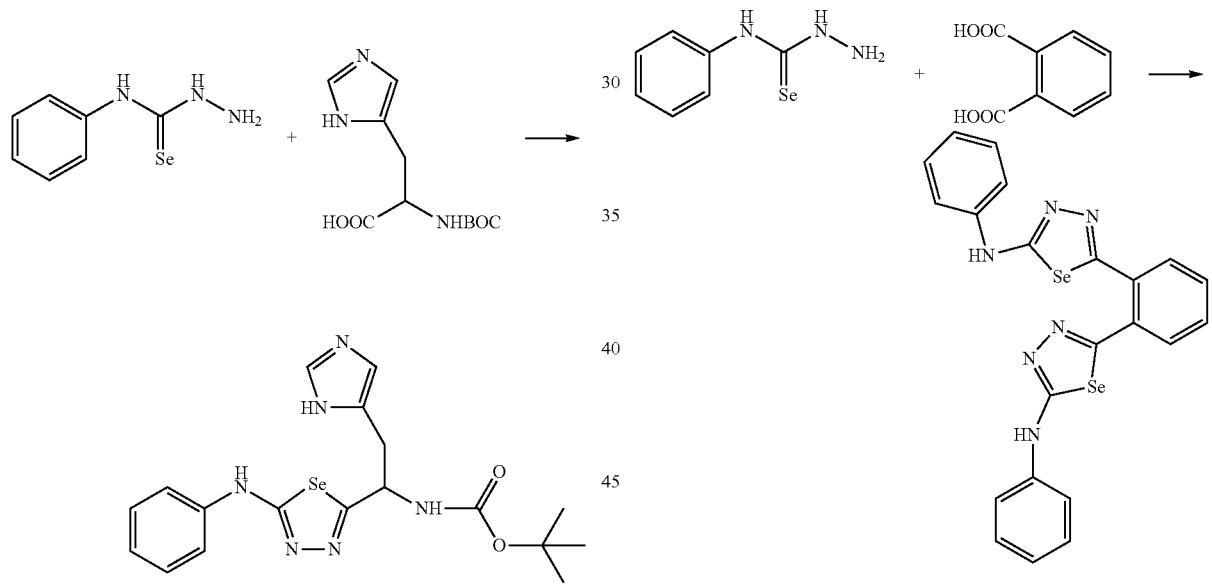

m/z 434 (100%, M+H$^+$)

$^1$H NMR (500 MHz) δ 10.34 (s, 1H), 8.06 (m, J=7.8 Hz, 5H), 7.59-7.46 (m, 3H), 4-3 (m, 3H), 1.4 (s, 9H)

5,5'-(1,3-phenylene)bis(N-phenyl-1,3,4-selenadiazol-2-amine) (Compound 27)

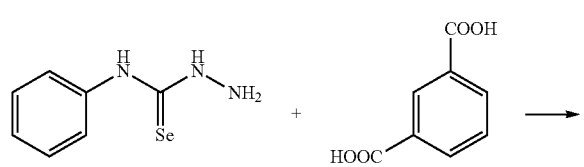

-continued

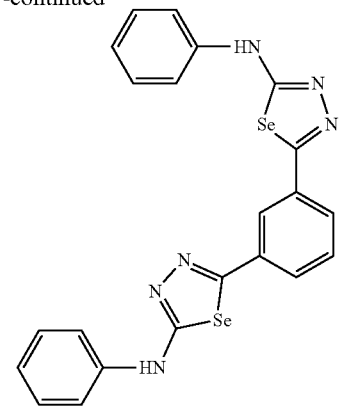

m/z 523 (100%, M+H$^+$)

$^1$H NMR (500 MHz) δ 9.97 (s, 2H), 8.4 (s, 1H), 8.1 (d, J=7.5, 2H), 7.62 (m, 5H), 7.33 (t, J=7.5 Hz, 4H), 6.99 (t, J=7.0 Hz, 2H)

5,5'-(1,2-phenylene)bis(N-phenyl-1,3,4-selenadiazol-2-amine) (Compound 28)

m/z 523 (100%, M+H$^+$)

$^1$H NMR (500 MHz) δ 9.97 (s, 2H), 8.1 (d, J=7.5, 2H), 7.62 (m, 6H), 7.33 (t, J=7.5 Hz, 4H), 6.9910 (t, J=7.0 Hz, 2H)

The 1,3,4-selenadiazole containing compounds described above showed antioxidant activity and protect PC12 cells (1000 per well) under anaerobic condition or in the presence of hydrogen peroxide. As shown in FIG. 1, 1,3,4-selenadiazole compounds (10000 nM) could protect and support cell growth under anaerobic condition for 3 days, whereas in the no compound control, cells did not survive.

Example 2

Further studies have shown that the selenadiazole containing KGA allosteric inhibitors have strong KGA inhibition (IC50<100 nM) and anti-tumor activity (IC50<100 nM for inhibiting A 549 lung cancer cells). The molecular structure of specific compounds is described as follows:

2.1 N-(6-(4-(5-(3-oxobenzo[d][1,2]selenazol-2(3H)-yl)-1,3,4-selenadiazol-2-yl)butyl)pyridazin-3-yl)-2-(3-(trifluoromethoxy)phenyl)acetamide

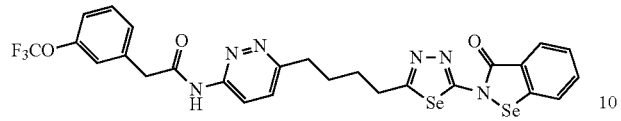

LRMS: m/z=682 [M+H]⁺

2.2 N-(5-(4-(6-(2-(3-oxobenzo[d][1,2]selenazol-2(3H)-yl)acetamido)pyridazin-3-yl)butyl)-1,3,4-selenadiazol-2-yl)picolinamide

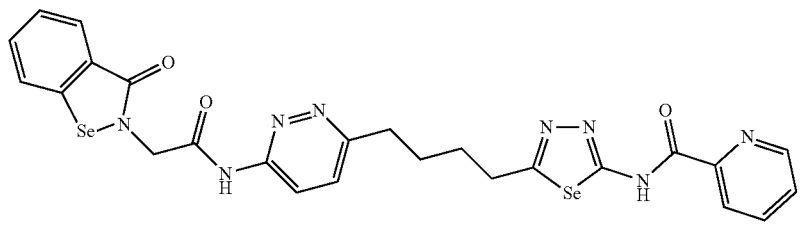 [SMILES: O=C(Cn1[se]c2ccccc2c1=O)Nc1ccc(CCCCc2nnc(NC(=O)c3ccccn3)[se]2)nn1]

LRMS: m/z=642 [M+H]⁺

2.3 N-(6-(4-(5-(3-(pyridin-2-yl)ureido)-1,3,4-selenadiazol-2-yl)butyl)pyridazin-3-yl)-2-(3-(trifluoromethoxy)phenyl)acetamide

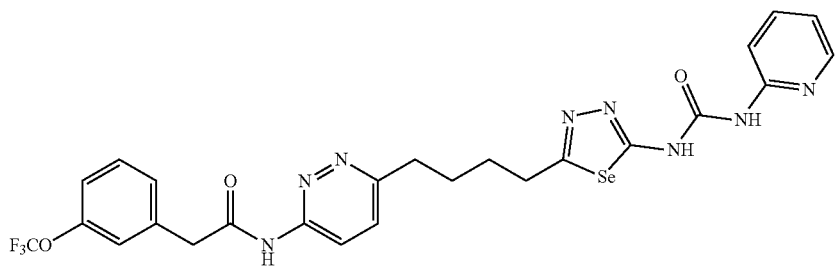 [SMILES: O=C(Cc1cccc(OC(F)(F)F)c1)Nc1ccc(CCCCc2nnc(NC(=O)Nc3ccccn3)[se]2)nn1]

LRMS: m/z=620 [M+H]⁺

2.4 N-(6-(4-(5-(3-(pyridin-3-yl)ureido)-1,3,4-selenadiazol-2-yl)butyl)pyridazin-3-yl)-2-(3-(trifluoromethoxy)phenyl)acetamide

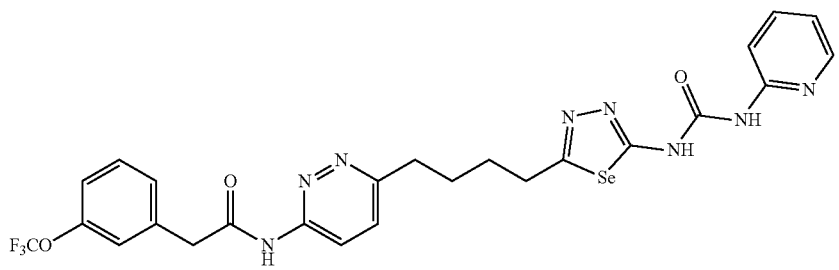 [SMILES: O=C(Cc1cccc(OC(F)(F)F)c1)Nc1ccc(CCCCc2nnc(NC(=O)Nc3ccccn3)[se]2)nn1]

LRMS: m/z=620 [M+H]⁺

2.5 N-(6-(4-(5-(3-(pyridin-4-yl)ureido)-1,3,4-selena-
diazol-2-yl)butyl)pyridazin-3-yl)-2-(3-(trifluo-
romethoxy)phenyl)acetamide

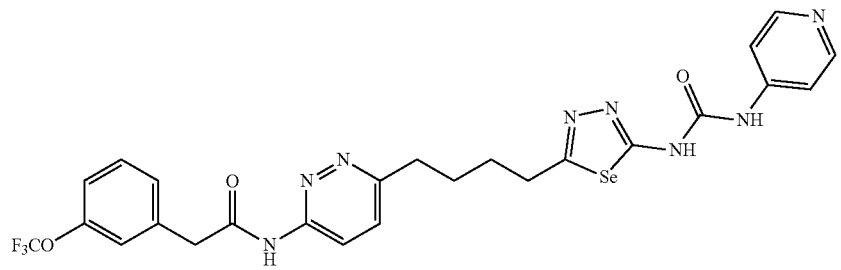 [SMILES: O=C(Cc1cccc(OC(F)(F)F)c1)Nc1ccc(CCCCc2nnc(NC(=O)Nc3ccncc3)[se]2)nn1]

LRMS: m/z=620 [M+H]$^+$ 2.6 2-(pyridin-2-yl)-N-(5-(4-((5-(2-(pyridin-2-yl)
acetamido)-1,3,4-selenadiazol-2-yl)amino)piperidin-
1-yl)-1,3,4-selenadiazol-2-yl)acetamide

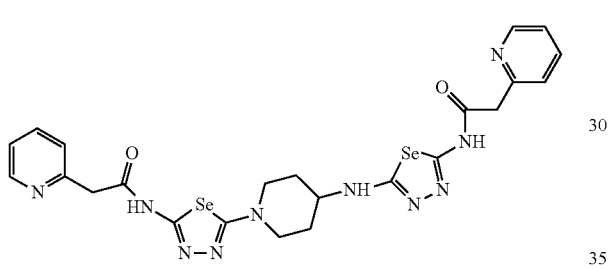

LRMS: m/z=632 [M+H]$^+$ 2.7 2-(3-oxobenzo[d][1,2]selenazol-2(3H)-yl)-N-(5-
(4-((5-(2-(3-oxobenzo[d][1,2]selenazol-2(3H)-yl)
acetamido)-1,3,4-thiadiazol-2-yl)amino)piperidin-1-
yl)-1,3,4-thiadiazol-2-yl)acetamide

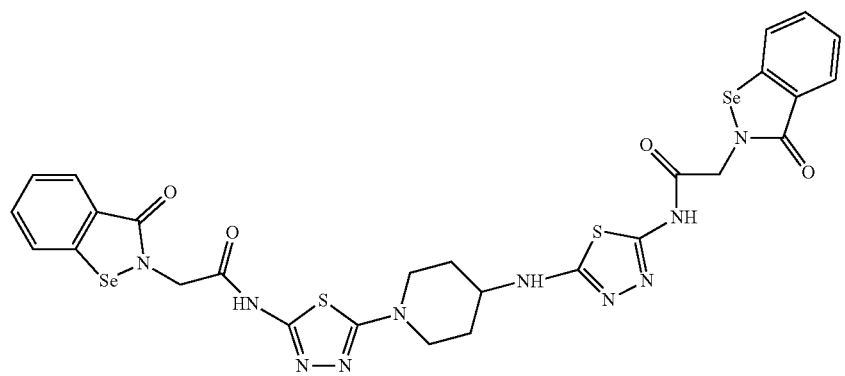 [SMILES: O=C(Cn1[se]c2ccccc2c1=O)Nc1nnc(NC2CCN(c3nnc(NC(=O)Cn4[se]c5ccccc5c4=O)s3)CC2)s1]

LRMS: m/z=776 [M+H]$^+$

2.8 2-(5-methoxy-1-methyl-1H-indol-3-yl)-N-(5-(4-((5-(2-(5-methoxy-1-methyl-1H-indol-3-yl)acetamido)-1,3,4-selenadiazol-2-yl)amino)piperidin-1-yl)-1,3,4-selenadiazol-2-yl)acetamide

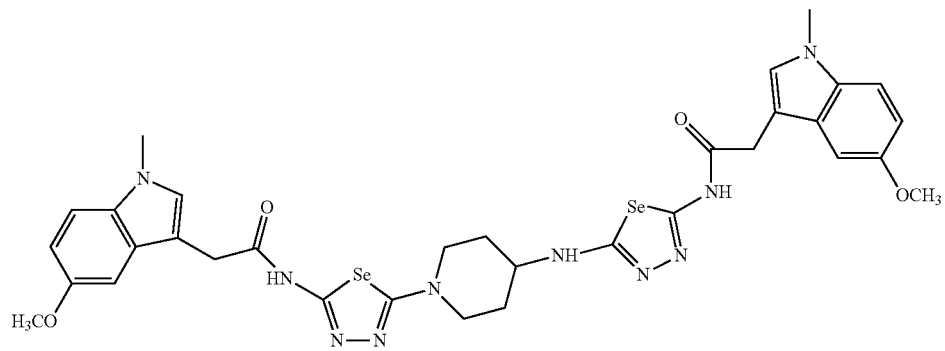 [SMILES: COc1ccc2c(c1)c(CC(=O)Nc1nnc(NC3CCN(c4nnc(NC(=O)Cc5cn(C)c6ccc(OC)cc56)[se]4)CC3)[se]1)cn2C]

LRMS: m/z=796 [M+H]+

2.9 (R)-2-(pyridin-2-yl)-N-(5-(3-(((5-(2-(pyridin-2-yl)acetamido)-1,3,4-selenadiazol-2-yl)oxy)methyl)pyrrolidin-1-yl)-1,3,4-selenadiazol-2-yl)acetamide

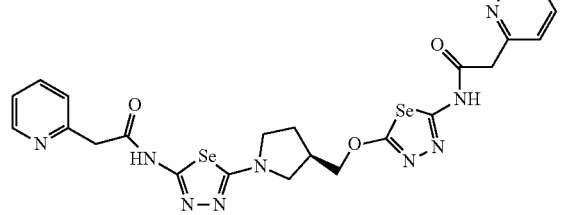

LRMS: m/z=633 [M+H]+

2.10 2-(pyridin-2-yl)-N-(5-(4-((5-(2-(pyridin-2-yl)acetamido)-1,3,4-selenadiazol-2-yl)oxy)piperidin-1-yl)-1,3,4-selenadiazol-2-yl)acetamide

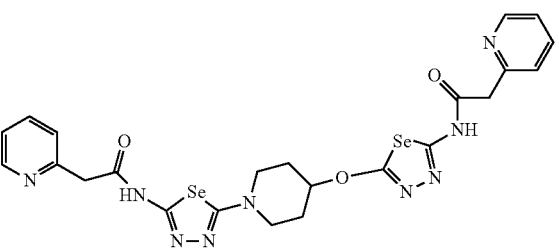 [SMILES: O=C(Cc1ccccn1)Nc1nnc(OC2CCN(c3nnc(NC(=O)Cc4ccccn4)[se]3)CC2)[se]1]

LRMS: m/z=633 [M+H]+

2.11 N,N'-(((1,3-phenylenebis(azanediyl))bis(methylene))bis(1,3,4-selenadiazole-5,2-diyl))bis(2-(pyridin-2-yl)acetamide)

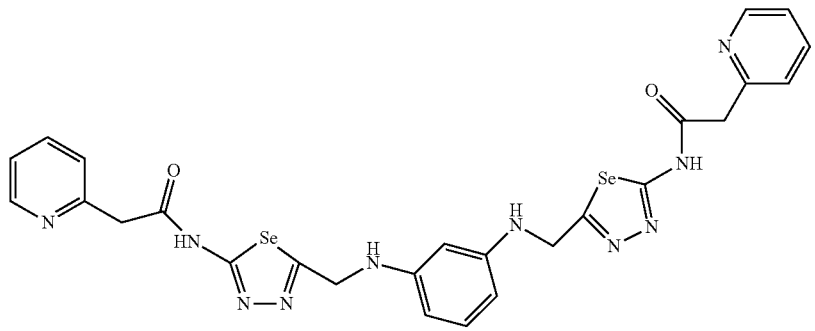 [SMILES: O=C(Cc1ccccn1)Nc1nnc(CNc2cccc(NCc3nnc(NC(=O)Cc4ccccn4)[se]3)c2)[se]1]

LRMS: m/z=668 [M+H]+

Besides, for testing the compounds get in example 1, the compound described as follow formula:

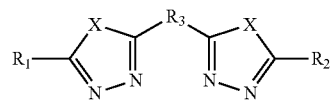

The results of such tests above are shown as follows:

| R1 | R2 | R3 | X | GDH IC$_{50}$ µM | KGA IC$_{50}$ µM | A549 IC$_{50}$ µM | A549 Max-INH % |
|---|---|---|---|---|---|---|---|
| (1-methylindol-3-yl)-CH$_2$-C(=O)-NH-CH$_3$ | —NH$_2$ | —CH$_2$CH$_2$SCH$_2$CH$_2$— | Se | >10 | 0.11 | 2.05 | 84 |
| (1-methylindol-3-yl)-CH$_2$-C(=O)-NH-CH$_3$ | —NH$_2$ | —CH$_2$CH$_2$SCH$_2$CH$_2$— | S | >10 | 0.14 | 9.7 | 55 |
| (1-methylindol-3-yl)-CH$_2$-C(=O)-NH-CH$_3$ | R$_1$ | —CH$_2$CH$_2$SCH$_2$CH$_2$— | Se | >10 | 0.027 | 0.16 | 90 |
| (1-methylindol-3-yl)-CH$_2$-C(=O)-NH-CH$_3$ | R$_1$ | —CH$_2$CH$_2$SCH$_2$CH$_2$— | S | >10 | 0.28 | 0.82 | 80 |
| (1-methylpyrrol-3-yl)-CH$_2$-C(=O)-NH-CH$_3$ | —NH$_2$ | —CH$_2$CH$_2$SCH$_2$CH$_2$— | Se | >10 | 0.21 | >10 | 40 |

-continued
| R1 | R2 | R3 | X | GDH IC$_{50}$ μM | KGA IC$_{50}$ μM | A549 IC$_{50}$ μM | A549 Max-INH % |
|---|---|---|---|---|---|---|---|
| 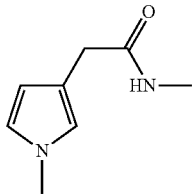 | —NH$_2$ | —CH$_2$CH$_2$SCH$_2$CH$_2$— | S | >10 | 0.57 | >10 | 0 |
| 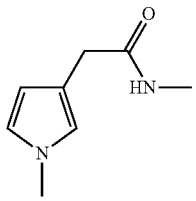 | R$_1$ | —CH$_2$CH$_2$SCH$_2$CH$_2$— | Se | >10 | 0.06 | 3.1 | 91 |
| 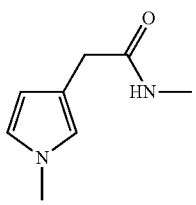 | R$_1$ | —CH$_2$CH$_2$SCH$_2$CH$_2$— | S | >10 | 0.13 | 6.5 | 80 |
| 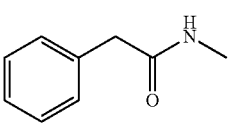 | —NH$_2$ | —CH$_2$CH$_2$SCH$_2$CH$_2$— | Se | >10 | 1.4 | 6.3 | 62 |
| 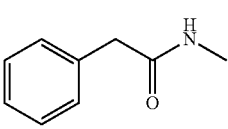 | —NH$_2$ | —CH$_2$CH$_2$SCH$_2$CH$_2$— | S | >10 | 2.5 | 9 | 50 |
| 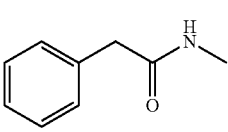 | R$_1$ | —CH$_2$CH$_2$SCH$_2$CH$_2$— | Se | >10 | 0.06 | 0.3 | 66 |
| 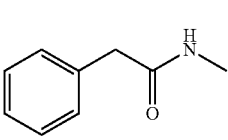 | R$_1$ | —CH$_2$CH$_2$SCH$_2$CH$_2$— | S | >10 | 0.13 | 0.87 | 75 |
| 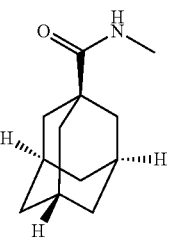 | —NH$_2$ | —CH$_2$CH$_2$SCH$_2$CH$_2$— | Se | >10 | 4 | >10 | 17 |

-continued

| R1 | R2 | R3 | X | GDH IC$_{50}$ μM | KGA IC$_{50}$ μM | A549 IC$_{50}$ μM | A549 Max-INH % |
|---|---|---|---|---|---|---|---|
| *N-methyl adamantane-1-carboxamide* | R$_1$ | —CH$_2$CH$_2$SCH$_2$CH$_2$— | Se | >10 | 1.9 | >10 | 17 |
| *N-methyl adamantane-1-carboxamide* | —NH$_2$ | —CH$_2$CH$_2$SCH$_2$CH$_2$— | Se | >10 | 0.3 | 4 | 56 |
| *3-(trifluoromethoxy)phenylacetamide-pyridazine-butyl-selenadiazole-pyridylacetamide* | | | | >10 | 0.001 | 0.017 | 77 |
| *3-(trifluoromethoxy)phenylacetamide-pyridazine-butyl-thiadiazole-pyridylacetamide* | | | | >10 | 0.002 | 0.04 | 70 |
| *3-(trifluoromethoxy)phenylacetamide-pyridazine-butyl-selenadiazole-(1-methylindol-3-yl)acetamide* | | | | >10 | 0.001 | 0.017 | 90 |
| *3-(trifluoromethoxy)phenylacetamide-pyridazine-butyl-selenadiazole-(5-methoxy-1-methylindol-3-yl)acetamide* | | | | >10 | 0.005 | 0.01 | 90 |

In summary, the above is only a preferred embodiment of the invention, equal changes and modification within the scope of the invention patent, should belong to the scope of the invention patent.

What is claimed is:
1. A 1, 3, 4-selenadiazole compound, represented by a general formula as follows:

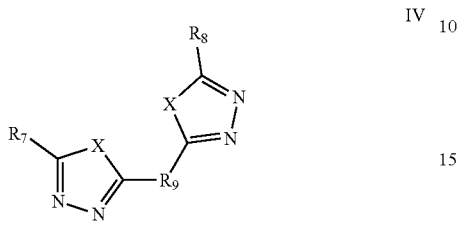

wherein:
$R_7$, $R_8$, $R_9$, X are selected as follows:

| $R_7$ | $R_8$ | $R_9$ | X |
|---|---|---|---|
| ![indole-CH2-C(O)-NH-CH3, N-methyl] | $-NH_2$ | $-CH_2CH_2SCH_2CH_2-$ | Se |
| ![indole-CH2-C(O)-NH-CH3, N-methyl] | ![indole-CH2-C(O)-NH-CH3, N-methyl] | $-CH_2CH_2SCH_2CH_2-$ | Se |
| ![pyrrole-CH2-C(O)-NH-CH3, N-methyl] | $-NH_2$ | $-CH_2CH_2SCH_2CH_2-$ | Se |
| ![pyrrole-CH2-C(O)-NH-CH3, N-methyl] | ![pyrrole-CH2-C(O)-NH-CH3, N-methyl] | $-CH_2CH_2SCH_2CH_2-$ | Se |
| ![phenyl-CH2-C(O)-NH-CH3] | $-NH_2$ | $-CH_2CH_2SCH_2CH_2-$ | Se |
| ![phenyl-CH2-C(O)-NH-CH3] | ![phenyl-CH2-C(O)-NH-CH3] | $-CH_2CH_2SCH_2CH_2-$ | Se |

-continued

| $R_7$ | $R_8$ | $R_9$ | X |
|---|---|---|---|
| 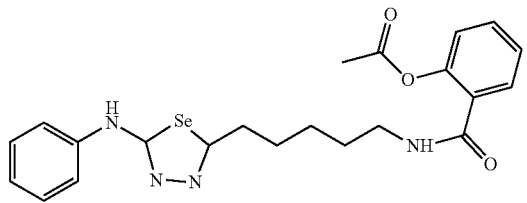 | —NH$_2$ | —CH$_2$CH$_2$SCH$_2$CH$_2$— | Se |
| 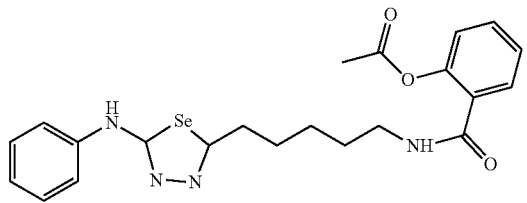 | 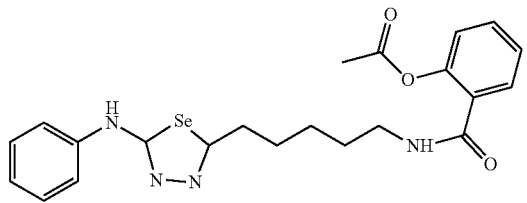 | —CH$_2$CH$_2$SCH$_2$CH$_2$— | Se |
| 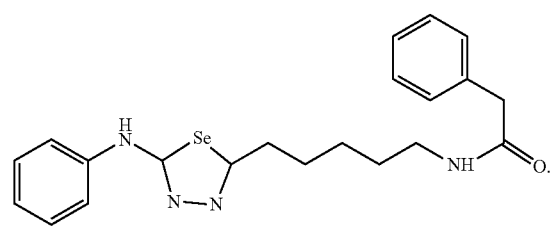 | —NH$_2$ | —CH$_2$CH$_2$SCH$_2$CH$_2$— | Se. |

2. A pharmaceutical composition containing the 1, 3, 4-selenadiazole compound of claim 1 and/or a pharmaceutically acceptable salt of the 1, 3, 4-selenadiazole compound and a pharmaceutically accepted carrier.

3. A 1, 3, 4-selenadiazole compound, selected from the group consisting of:

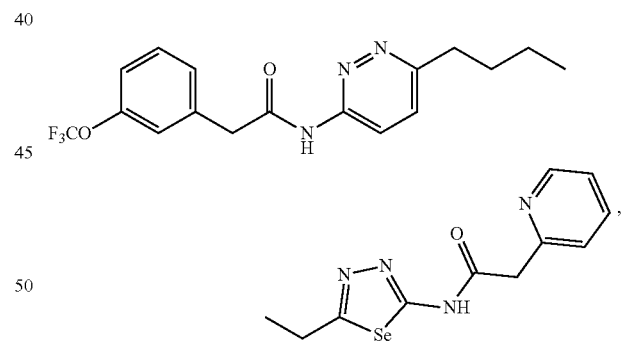

and

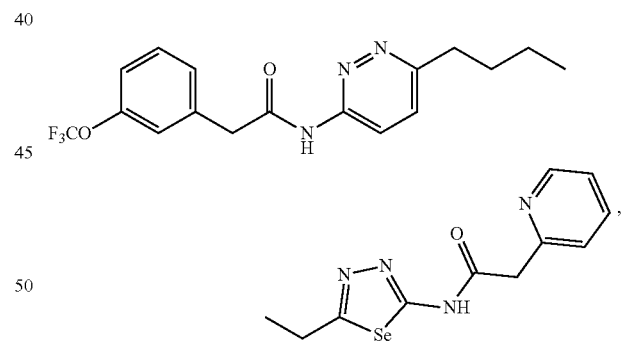

4. A 1, 3, 4-selenadiazole compound, selected from the group consisting of:

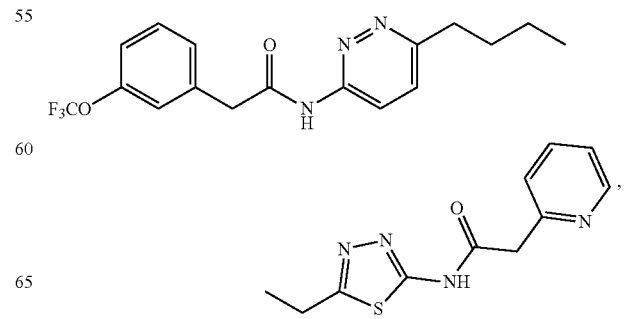

-continued

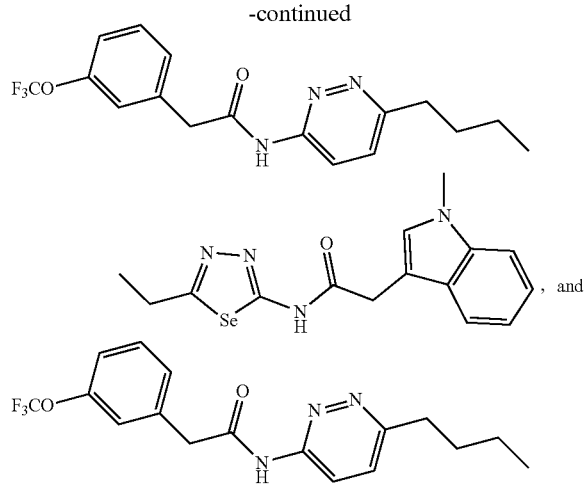

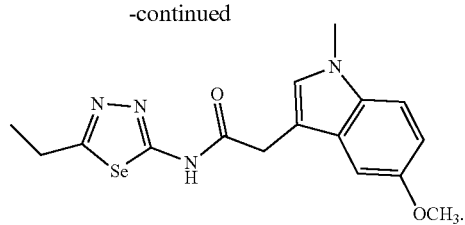

5. A method of applying the 1, 3, 4-selenadiazole compound of claim 1, for cancer therapeutics such as liver cancer and pancreatic cancer.

6. The method of claim 5 wherein the method is used in combination with at least one selected from the group consisting of rapamycin, FK506, bacteriocin D, adriamycin, paclitaxel, mitomycin, gemcitabine, 5 fluorouracil, pinocanoic acid, and their derivatives.

* * * * *